(12) United States Patent
Yeatts

(10) Patent No.: US 11,628,291 B2
(45) Date of Patent: Apr. 18, 2023

(54) WIRELESS DIAGNOSTIC SYSTEM FOR INDIRECT FLOW MEASUREMENT IN ARTIFICIAL HEART PUMPS

(71) Applicant: Dale J. Yeatts, Woodland Hills, CA (US)

(72) Inventor: Dale J. Yeatts, Woodland Hills, CA (US)

(73) Assignee: Dale J. Yeatts, Woodland Hills (CA)

( * ) Notice: Subject to any disclaimer, the term of this patent is extended or adjusted under 35 U.S.C. 154(b) by 1019 days.

(21) Appl. No.: 16/161,423

(22) Filed: Oct. 16, 2018

(65) Prior Publication Data

US 2019/0111197 A1 Apr. 18, 2019

Related U.S. Application Data

(63) Continuation of application No. 15/353,926, filed on Nov. 17, 2016, now Pat. No. 10,130,743.

(Continued)

(51) Int. Cl.
*A61M 60/148* (2021.01)
*G08B 21/18* (2006.01)
(Continued)

(52) U.S. Cl.
CPC ........ *A61M 60/148* (2021.01); *A61M 60/178* (2021.01); *A61M 60/216* (2021.01); *A61M 60/411* (2021.01); *A61M 60/508* (2021.01); *A61M 60/585* (2021.01); *A61M 60/592* (2021.01); *A61M 60/876* (2021.01); *A61M 60/88* (2021.01); *G08B 21/18* (2013.01);
(Continued)

(58) Field of Classification Search
CPC ..... G08B 21/18; G06F 19/3412; A61M 1/122
See application file for complete search history.

(56) References Cited

U.S. PATENT DOCUMENTS 7,942,824 B1 * 5/2011 Kayyali ............. A61B 5/14551
600/538
2003/0045772 A1 3/2003 Reich et al.
(Continued)

FOREIGN PATENT DOCUMENTS

EP       3 053 613 A1    8/2016
WO    WO 2015/048920 A1  4/2015

OTHER PUBLICATIONS

International Preliminary Report on Patentability, Chapter II, for International Patent Application No. PCT/IB2016/056938 dated Feb. 15, 2018, 30 pages.
(Continued)

*Primary Examiner* — Lisa E Peters
(74) *Attorney, Agent, or Firm* — Alston & Bird LLP

(57) ABSTRACT

Systems, apparatuses, and methods are disclosed for optimizing management of one or more implanted artificial heart pumps. An example method includes wirelessly retrieving, via one or more portable diagnostic devices, data regarding the one or more implanted artificial heart pumps. The example method further includes analyzing, by a server device, performance characteristics of the one or more implanted artificial heart pumps based on the retrieved data. The example method further includes causing rendering of the performance characteristics. Corresponding apparatuses and computer program products are contemplated.

20 Claims, 6 Drawing Sheets

Related U.S. Application Data

(60) Provisional application No. 62/256,659, filed on Nov. 17, 2015.

(51) Int. Cl.

| | | |
|---|---|---|
| *G16H 40/40* | (2018.01) | |
| *G16Z 99/00* | (2019.01) | |
| *A61M 60/178* | (2021.01) | |
| *A61M 60/216* | (2021.01) | |
| *A61M 60/411* | (2021.01) | |
| *A61M 60/876* | (2021.01) | |
| *A61M 60/88* | (2021.01) | |
| *A61M 60/592* | (2021.01) | |
| *A61M 60/508* | (2021.01) | |
| *A61M 60/585* | (2021.01) | |
| *H04W 4/70* | (2018.01) | |
| *H04L 67/12* | (2022.01) | |

(52) U.S. Cl.
CPC ............ *G16H 40/40* (2018.01); *G16Z 99/00* (2019.02); *A61M 2205/3515* (2013.01); *A61M 2205/3523* (2013.01); *A61M 2205/3553* (2013.01); *A61M 2205/3592* (2013.01); *A61M 2205/70* (2013.01); *H04L 67/12* (2013.01); *H04W 4/70* (2018.02)

(56) References Cited

U.S. PATENT DOCUMENTS

| | | | | |
|---|---|---|---|---|
| 2003/0069465 | A1* | 4/2003 | Benkowski | A61M 60/422 600/16 |
| 2004/0039243 | A1 | 2/2004 | Beamson et al. | |
| 2009/0058635 | A1* | 3/2009 | LaLonde | A61B 5/747 340/539.11 |
| 2009/0063187 | A1* | 3/2009 | Johnson | H04W 48/18 705/2 |
| 2009/0149951 | A1 | 6/2009 | Sugiura et al. | |
| 2009/0156885 | A1* | 6/2009 | Morello | A61M 60/50 600/16 |
| 2010/0249882 | A1 | 9/2010 | Houben | |
| 2011/0019595 | A1 | 1/2011 | Magar et al. | |
| 2011/0160516 | A1* | 6/2011 | Dague | A61M 60/871 600/16 |
| 2011/0270579 | A1 | 11/2011 | Watson et al. | |
| 2012/0078031 | A1 | 3/2012 | Burke et al. | |
| 2012/0172657 | A1* | 7/2012 | Marseille | A61M 60/871 600/16 |
| 2012/0245680 | A1 | 9/2012 | Masuzawa et al. | |
| 2013/0310631 | A1 | 11/2013 | Lee et al. | |
| 2013/0324929 | A1 | 12/2013 | Mochizuki et al. | |
| 2014/0275727 | A1 | 9/2014 | Bonde et al. | |
| 2015/0022375 | A1* | 1/2015 | Lee | G08C 23/04 340/870.28 |
| 2016/0080365 | A1* | 3/2016 | Baker | G16H 40/67 726/4 |
| 2016/0263299 | A1 | 9/2016 | Xu et al. | |

OTHER PUBLICATIONS

Written Opinion of the International Preliminary Examining Authority, Chapter II, for International Patent Application No. PCT/IB2016/056938 dated Dec. 22, 2017, 9 pages.
International Search Report and Written Opinion for International Patent Application No. PCT/IB2016/056938 dated Mar. 29, 2017, 20 pages.
Invitation to Pay Additional Fees/Partial International Search Report for International Application No. PCT/IB2016/056938 dated Feb. 8, 2017.
Salamonsen et al.; "Response of Rotary Blood Pumps to Changes in Preload and Afterload at a Fixed Speed Setting Are Unphysiological When Compared with the Natural Heart"; 35 Artificial Organs E47-E53 (2011).
Belkin Corporation, Wireless G USB Network Adapter, User Manual, 2005, pp. 1-40.
MicroMed Cardiovascular Inc, MicroMed Cardiovascular's HeartAssist 5TM Goes Wireless, 2012, p. 1.
HeartWare Inc, HeartWare® Ventricular Assist System, Instructions for Use, pp. 1-96.
"Ventricular assist device (VAD) trends." [Retrieved Jun. 8, 2017]. Retrieved from the Internet: <URL: https://campaign.optum.com/content/dam/optum/resources/whitePapers/Ventricular-Assist-Device-Trends-White-Paper.pdf> (dated 2012), 6 pages.
Ayre, P.J. et al. "Sensorless flow and head estimation in the VentrAssist rotary blood pump." Artificial Organs, 24(8), (2000) pp. 585-588.
Boyle, A.J. et al. "Clinical outcomes for continuous-flow left ventricular assist device patients stratified by pre-operative INTERMACS classification." The Journal of Heart and Lung Transplantation, 30(4), (2011) pp. 402-407.
Cannon, A. et al. "Variability in infection control measures for the percutaneous lead among programs implanting long-term ventricular assist devices in the United States." Progress in Transplantation, 22(4), (2012), pp. 351-359.
Chaudhry, S.I. et al. "Telemonitoring in patients with heart failure." Phillips C.O. The New England Journal of Medicine, 363(24), (2010), pp. 2301-2309.
Desai, A.S. "Home monitoring heart failure care does not improve patient outcomes: looking beyond telephone-based disease management." Circulation, 125(6), (2012), pp. 828-836.
Farrar, D.J. et al. "Design features, developmental status, and experimental results with the Heartmate III centrifugal left ventricular assist system with a magnetically levitated rotor." ASAIO Journal, 53(3), (2007), pp. 310-315.
Forest, S.J. et al.. "Readmissions after ventricular assist device: etiologies, patterns, and days out of hospital." The Annals of Thoracic Surgery, 95(4), (2013), pp. 1276-1281.
Funakubo, A. et al. "Flow rate and pressure head estimation in a centrifugal blood pump." Artificial Organs, 26(11), (2002), pp. 985-990.
Goldstein, D.J. et al. "Contemporary continuous flow devices: how much does it cost to keep a patient on support for one year?" The Journal of Heart and Lung Transplantation, 31(4S), (2012), S85.
Hasin, T. et al. "Readmissions after implantation of axial flow left ventricular assist device." The Journal of the American College of Cardiology, 61(2), (2013), pp. 153-163.
Inglis, S.C. et al. "Structured telephone support or telemonitoring programmes for patients with chronic heart failure." The Cochrane Database of Systematic Reviews, 4(8), (2010), CD007228.
Kirklin, J.K. et al. "Sixth INTERMACS annual report: a 10,000-patient database." The Journal of Heart and Lung Transplantation, 33(6), (2014), pp. 555-564.
Kitamura, T. et al. "Physical model-based indirect measurements of blood pressure and flow using a centrifiigal pump." Artificial Organs, 24(8), (2000), pp. 589-593.
Medvedev, A.L. et al. "Unlocking the box: basic requirements for an ideal ventricular assist device controller." Expert Review of Medical Devices, 14(5), (2017), pp. 393-400.
Miller, L.W. "Left ventricular assist devices are underutilized." Circulation, 123(14), (2011), pp. 1552-1558.
Miller, L.W. et al. "Cost of ventricular assist devices: can we afford the progress?" Circulation, 127(6), (2012), pp. 743-748.
Mulloy, D.P. et al. "Orthotopic heart transplant versus left ventricular assist device: a national comparison of cost and survival." The Journal of Thoracic and Cardiovascular Surgery, 145(2), (2013), pp. 566-573.
Nakata, K. et al. "Control system for an implantable rotary blood pump." ASAIO Journal, 45(2), (1999), 160.
Ogawa, D. et al. "Indirect flow rate estimation of the NEDO PI Gyro Pump for chronic BVAD experiments." ASAIO Journal, 52(3), (2006), pp. 266-271.
Oz, M.C. et al. "Left ventricular assist devices as permanent heart failure therapy: the price of progress." Annals of Surgery, 238(4), (2003) pp. 577-585.

(56) References Cited

OTHER PUBLICATIONS

Pagani, F.D. "Continuous-flow rotary left ventricular assist devices with "3rd generation" design." Seminars in Thoracic and Cardiovascular Surgery, 20(3), (2008), pp. 255-263.
Rogers, J.G. et al. "Costeffectiveness analysis of continuous-flow left ventricular assist devices as destination therapy." Circulation. Heart Failure, 5(1), 10-16.
Rose, E.A. et al. "Long-term use of a left ventricular assist device for end-stage heart failure." The New England Journal of Medicine, 345(29), (2001), pp. 1435-1443.
Salamonsen, R.F. et al. "Theoretical foundations of a Starling-like controller for rotary blood pumps." Artificial Organs, 36(9), (2012), pp. 787-796.
Slaughter, M.S. et al. "Advanced heart failure treated with continuous-flow left ventricular assist device." The New England Journal of Medicine, 261(23), (2009), pp. 2241-2251.
Slaughter, M.S. et al. "Temporal changes in hospital costs for left ventricular assist device implantation." Journal of Cardiac Surgery, 26(5), (2011), 535-541.
Smedira, N.G. et al. "Unplanned hospital readmissions after HeartMate II implantation." The Journal of the American College of Cardiology: Heart Failure, 1(1), (2013), pp. 31-39.
Stewart, G.C. et al. "Keeping left ventricular assist device acceleration on track." Circulation, 123(14), (2011), pp. 1559-1568.
Tsiouris, A. et al. "Factors deteimining post-operative readmissions after left ventricular assist device implantation." The Journal of Heart and Lung Transplantation, 33(10), (2014), pp. 1041-1047.
Tsukiya, T. et al. "Application of indirect flow rate measurement using motor driving signals to a centrifugal blood pump with an integrated motor." Artificial Organs, 25(9), (2001), pp. 692-696.
Tsukiya, T. et al. "Use of motor current in flow rate measurement for the magnetically suspended centrifugal blood pump." Artificial Organs, 21(5), (1997), pp. 396-401.
Office Action for U.S. Appl. No. 15/353,926 dated Mar. 2, 2017.
Office Action for U.S. Appl. No. 15/353,926 dated Aug. 15, 2017.
Office Action for U.S. Appl. No. 15/353,926 dated Jan. 12, 2018.
Notice of Allowance for U.S. Appl. No. 15/353,926 dated Jul. 17, 2018.

\* cited by examiner

WIRELESS DIAGNOSTIC SYSTEM FOR INDIRECT FLOW MEASUREMENT IN ARTIFICIAL HEART PUMPS

CROSS-REFERENCE TO RELATED APPLICATIONS

This application is a continuation of U.S. application Ser. No. 15/353,926 (published as U.S. 2017/0136164), filed Nov. 17, 2016, which application claims the benefit of U.S. Provisional Patent Application No. 62/256,659, filed Nov. 17, 2015, the entire contents of each of which are incorporated herein by reference.

TECHNOLOGICAL FIELD

Example embodiments of the present invention relate generally to implanted artificial heart pumps that indirectly measure flow and, more particularly, to methods and apparatuses for acquiring and analyzing data from implanted artificial heart pumps.

BACKGROUND

In the field of artificial heart-assist technology, advances in the mechanical design of implantable circulatory pumps have been complemented by similar improvements in their external control units. These units have been designed to be increasingly sensitive to the dynamic interaction between the blood pump and the patient's heart to better provide end-users with real-time information that can be used to measure the machine's performance under particular operating parameters.

While blood flow measurement through the artificial heart pump is most accurate when received directly from an actual probe inserted into the outflow track of the pump conduit, implanted sensors that maintain direct contact with blood can perturb its flow and activate factors within the blood that increase the risk of blood clot formation. These clots can disturb motor blade performance and cause complete machine malfunction. When this occurs, total pump replacement may be required, mandating a high-risk open chest surgery. In the United States, direct flow heart pumps are limited, by regulation, to investigational use only. Only indirect flow measurement technology is approved by the Food and Drug Administration (FDA) for widespread therapeutic use in the United States, and heart pump engineering trends are producing new indirect-flow prototypes that are more reliable and durable than previous iterations because they continue to reduce the number of high resistance areas in the interface between the pump's surface and the patient's blood. Currently, the newest "$3^{rd}$ generation" heart pump models all estimate flow indirectly without the use of direct sensor components.

As an alternative to the placement of direct measurement sensors in the body, heart pump performance can be indirectly estimated using engineering formulas that relate motor torque, fluid flow rate, and the pressure of fluid moved by the motor at a particular speed. For most heart pumps, the speed of the moving motor blades that propel blood forward through the heart is the one fixed variable that can be adjusted by the end-user. Because the motors are based on brushless, direct-current design, the torque they generate is directly proportional to the power they consume in electrical current. By measuring the real-time power demands of a pump, the torque variable can be estimated. Once both torque and speed variables are known, flow and pump head pressure (the difference in pressure between the inflow and outflow portions of the pump) can be estimated. Heart pumps differ from each other in certain design characteristics that cause them to react idiosyncratically when they consume power to propel blood through the circulation. As a result, each pump utilizes its own proprietary program to convert current usage to torque and to calculate the effects of blood viscosity on the motor.

In its current design configuration, to obtain real-time flow measurements for heart pump technology based on indirect flow estimations, a portable controller must be attached to a larger monitor. Depending on the manufacturer, the monitor contains the software to display continuous flow data, either numerically alone or both numerically and in a waveform format. These monitors are cost prohibitive for individual patient use, and only intended for diagnosing and managing heart pump-related issues in hospital or clinic facilities where expert personnel are available to titrate the motor speed to optimal flow dynamics. After hospital discharge, and between outpatient clinic visits every several months, the heart pump device functions according to the most recent settings and cannot respond dynamically to any change in the patient's physiology.

The inability to remotely discern heart pump operating variables, characterize their trends over time, and assess their interactions with the native heart represents a missed opportunity to better utilize this transformative technology. The infrequent contact between expert and patient due to logistical constraints results in a necessarily passive heart pump utilization strategy that precludes maximal titration of the heart pump to respond to the patient's changing circulatory status. High motor rotating speeds can cause greater emptying of the left heart than physiologically appropriate and precipitate suction problems between the inlet port and the heart wall, especially in low volume situations. Because patients receive limited supervision as outpatients, clinicians and engineers may enter long-term speed settings that are lower than optimal to provide a safety margin against heart pump suction complications. However, this added safety is gained at the cost of the pump's full potential to support the heart, which could be achieved with higher operating speeds. This is undesirable because heart failure is a dynamic process: either the patient's native circulatory function is improving with the support of the pump and gradually recovering lost function or it is further deteriorating as a result of intrinsic, irreversible disease—opposite trends that require divergent heart pump management strategies. Level of patient daily activity and hydration status are other variable factors that can influence the optimal operating target speed of a particular heart pump.

A device with the capability to remotely monitor disease progression in patients with implanted artificial heart pumps, including those using the indirect-flow measurement algorithms on which the great majority of heart pumps operate, could form the cornerstone of a more nuanced heart pump management strategy by facilitating expert oversight of the patient and the implanted artificial heart pump in a non-clinical setting. A system employing such a device could utilize software packages to create dynamic models of the heart pump flow patterns and the patient's cardiac performance to guide fine-tuning of speed adjustments. Such an innovation would be useful for ensuring the most satisfactory pump performance and identifying problem trends requiring early intervention to prevent severe complications, including hospitalization or death.

BRIEF SUMMARY

Accordingly, example embodiments described herein demonstrate methods and apparatuses for the remote monitoring and assessment of implantable artificial heart pumps, including those that indirectly measure flow. Some example embodiments rely on indirect measurement of blood flow and blood pressure characteristics to guide decision-making regarding the optimum operating parameters of the machine. Because many implantable artificial heart pumps are designed for long-term use in the outpatient setting, example embodiments described herein greatly expand the oversight capability and permit more data-driven optimization of indirect flow measurement blood pumps without added interference with recipients' quality of life and independence.

In a first aspect of the invention, a diagnostic device is contemplated that will attach to the site on the heart pump controller at the connector location designed by the manufacturer to interface directly with a supplemental monitor used in clinical settings. In normal outpatient operations, this port is either not utilized or supports a redundant connection to the external battery pack. However, as described below, this port may be used in some example embodiments to continuously query the internal heart pump's external portable controller to gather data on power consumption and other operating variables estimated by the controller using manufacturer-specific algorithms. In some embodiments, the transfer of data from the heart pump to the diagnostic device may be restricted to a single direction to protect the integrity of the system by ensuring that changes to the operating speed can only occur with manual adjustment. As described below, the diagnostic device may also be designed to record problem-event alarms that are activated by the pump controller when the estimated flow either exceeds or falls below manufacturer-specified parameters. Currently, this real-time data is inaccessible to expert decision makers during the interval period that a patient is outside of a formal medical environment.

In another aspect of the invention, the diagnostic device may contain a wireless transmitter to send heart pump performance data to remote monitoring servers for processing and analysis. The transmission technology may, in some embodiments, have the capability to communicate across multiple wireless bandwidths, including low-power radio frequencies and those allocated by the Federal Communications Commission (FCC) for exclusive medical usage. This aspect of the invention, for the first time, allows indirect flow measurements and other pump performance characteristics to be remotely retrieved. It should be understood that in some embodiments, the heart pump controller may be itself be designed to carry out wireless transmissions, and in such embodiments, the heart pump controller can transfer the heart pump performance data to the remote monitoring servers without the need to utilize a separate diagnostic device as an intermediary.

In another aspect of the invention, a receiving computer server at a remote site location may receive the transmitted signals from the device and use a software application to process the heart pump performance and estimate additional physiological variables using mathematical algorithms. The receiving computer may, in this regard, also arrange the data in an integrated visual platform that provides more clinical information than the raw engineering numbers heretofore generated by manufacturers' software and may present that information in a more intuitive fashion for expert end-users. As a result, this aspect of the invention may better promote best-practice clinical decisions regarding heart pump use than currently exist for indirect flow measurement machines.

The above summary is provided merely for purposes of summarizing some example embodiments to provide a basic understanding of some aspects of the invention contemplated herein. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having thus described some example embodiments in general terms, reference will now be made to the accompanying drawings, which are not necessarily drawn to scale.

Figure 1:
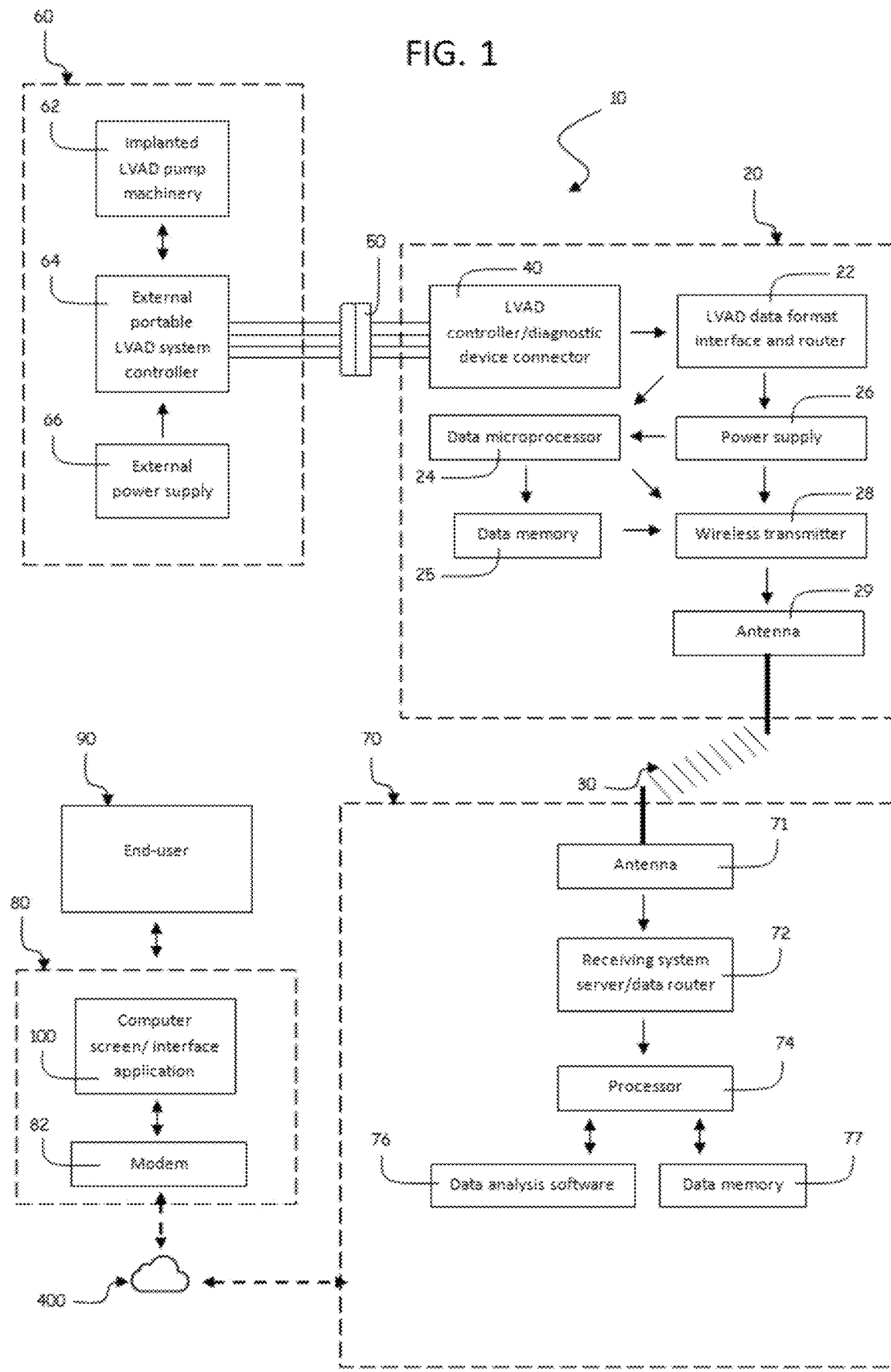

FIG. 1 provides a schematic block diagram of an example system comprising diagnostic device in contact with a ventricular assist device and a remote server, in accordance with example embodiments described herein.

FIGS. 2A, 2B, 2C, and 2D illustrate a series of perspective views of an example wireless diagnostic device having a hub connector designed to interface with a certain proprietary heart pump controller, in accordance with example embodiments described herein.

FIGS. 3A, 3B, 3C, and 3D provides a multi-dimensional view of another example wireless diagnostic device with a hub connector designed to interface with an alternate proprietary heart pump controller, in accordance with example embodiments described herein.

Figure 4:
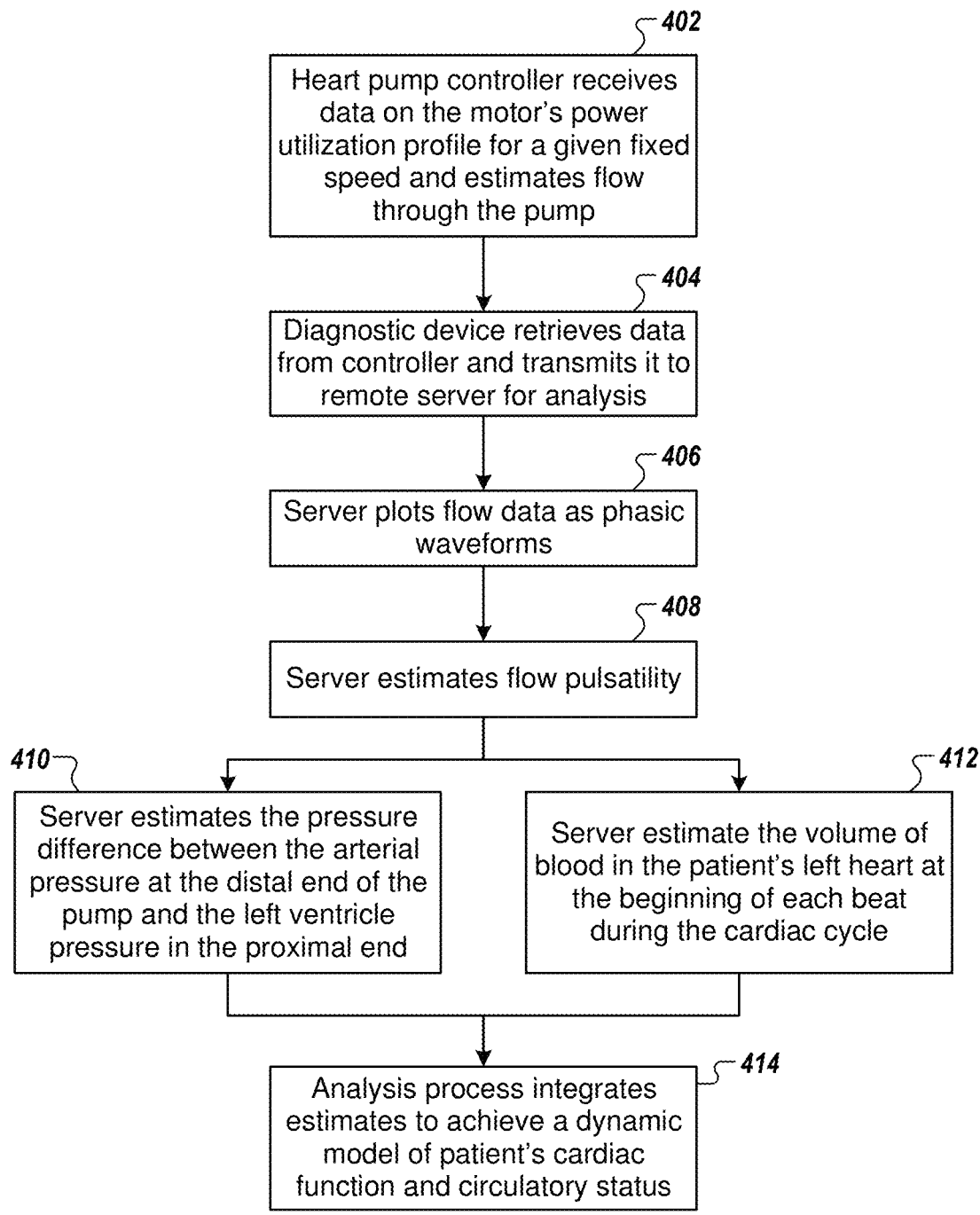

FIG. 4 illustrates a flowchart describing example operations for analyzing data retrieved from an implanted artificial heart pump that indirectly measures flow by a diagnostic device, in accordance with example embodiments described herein.

Figure 5:
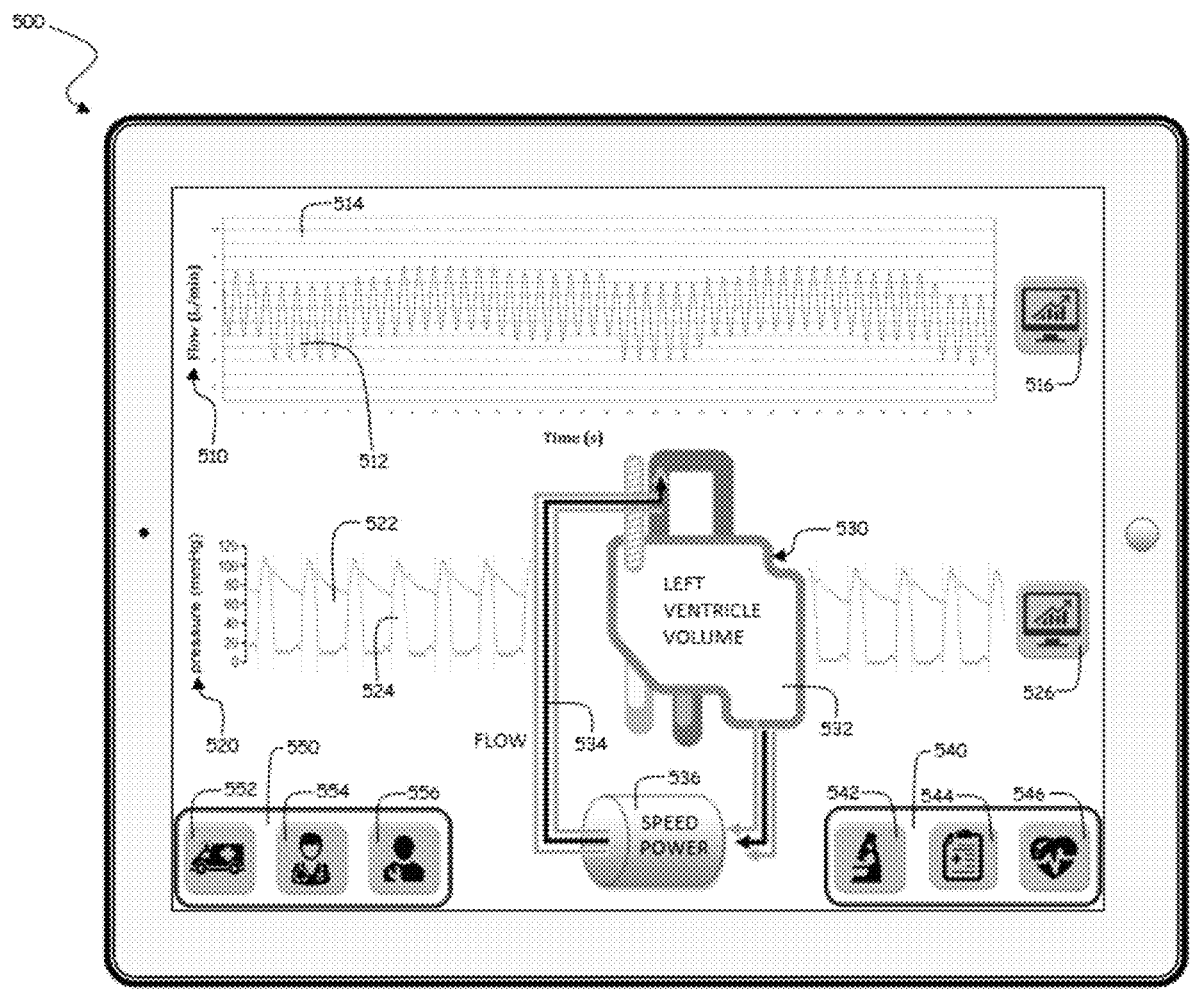

FIG. 5 provides an illustration of a user interface provided by an example remote heart pump monitoring application that provides a visual dashboard for assessing data acquired from the heart pump and patient-related physiological estimates, in accordance with example embodiments described herein.

Figure 6:
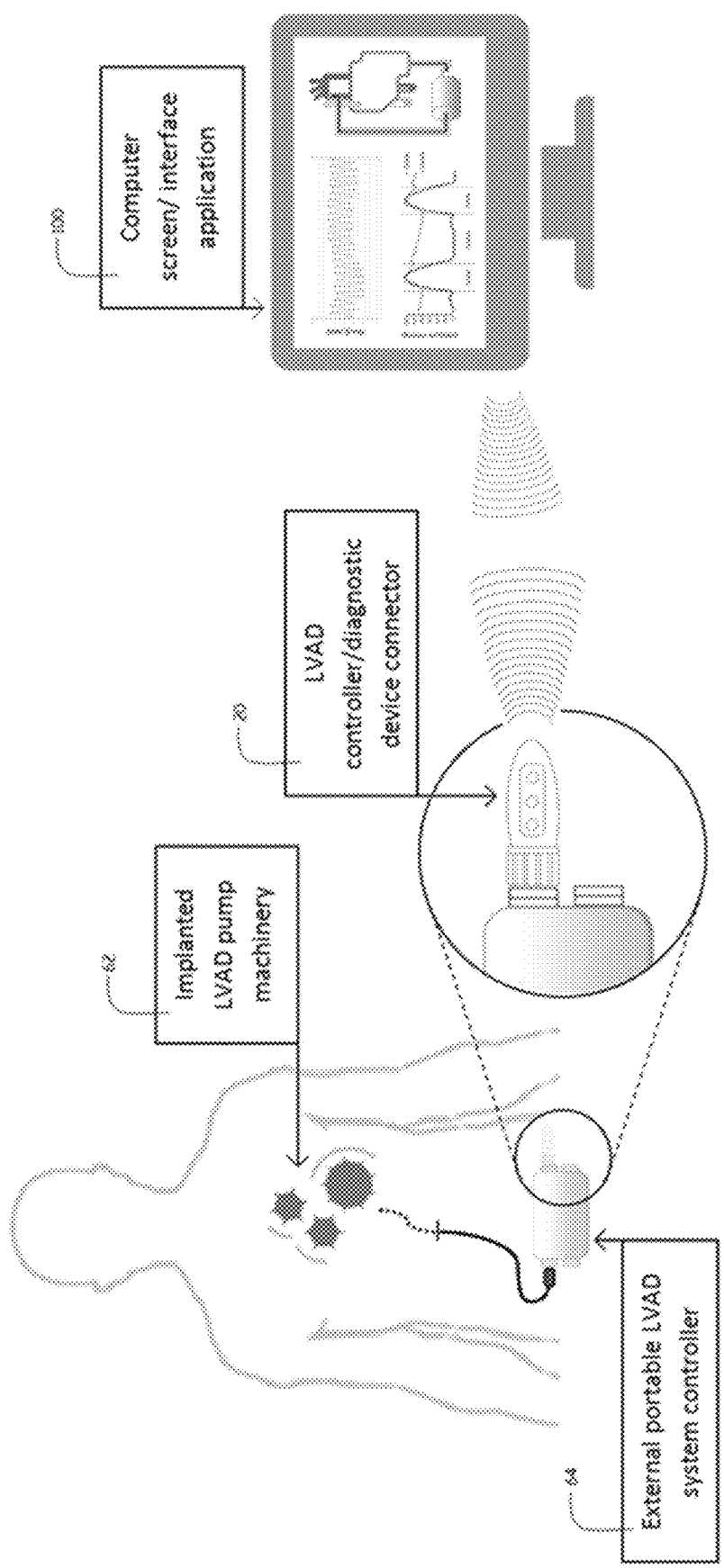

FIG. 6 provides an illustration of a high-level system diagram in accordance with example embodiments described herein.

DETAILED DESCRIPTION

Some example embodiments will now be described more fully with reference to the accompanying drawings, in which some, but not all, contemplated embodiments are shown. Indeed, the contemplated inventions may be embodied in many different forms and should not be construed as limited to the example embodiments set forth herein; rather, these example embodiments are provided so that this disclosure will satisfy applicable legal requirements. Like numbers refer to like elements throughout. As used herein, "data," "content," "information," and similar terms may be used interchangeably to refer to data capable of being transmitted, received, and/or stored in accordance with embodiments of the present invention. Thus, use of any such terms should not be taken to limit the spirit or scope of the present invention.

As used herein, a "computer-readable storage medium," which refers to a non-transitory physical storage medium (e.g., a volatile or non-volatile memory device), can be differentiated from a "computer-readable transmission medium," which refers to an electromagnetic signal.

As used herein, a "processor," which may comprise, for example, microprocessor 24, processor 74, or the like, may be embodied in a number of different ways. For example, the processor may be embodied as one or more of various hardware processing means such as a co-processor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like. As such, in some embodiments, the processor may include one or more processing cores configured to perform independently. A multi-core processor may enable multiprocessing within a single physical package. Additionally or alternatively, the processor may include one or more processors configured in tandem via the bus to enable independent execution of instructions, pipelining, and/or multithreading.

In example embodiments, the processor may be configured to execute instructions stored in a memory (e.g., memory devices 25 or 77) or otherwise accessible to the processor. Alternatively or additionally, the processor may be configured to execute hard-coded functionality. Thus, for example, when the processor is embodied as an ASIC, FPGA, or the like, the processor may comprise specifically configured hardware for conducting operations described herein. Alternatively, as another example, when the processor is embodied as an executor of software instructions, the instructions may specifically configure the processor to perform the algorithms and/or operations described herein when the instructions are executed. The processor may include, among other things, a clock, an arithmetic logic unit (ALU), and logic gates configured to support operation of the processor.

In turn, as used herein a "memory," such as memory devices 25 and 77 may be non-transitory and may include, for example, one or more volatile and/or non-volatile memories. In other words, for example, the memory may be an electronic storage device (e.g., a computer readable storage medium) comprising gates configured to store data (e.g., bits) that may be retrievable by a machine (e.g., a computing device like the processor). The memory may be configured to store information, data, content, applications, instructions, or the like, for enabling an apparatus to carry out various functions in accordance with an example embodiments described herein. For example, the memory could be configured to buffer input data for processing by the processor. Additionally or alternatively, the memory could be configured to store instructions for execution by the processor.

Having discussed some example terminology used herein, some example embodiments of the present invention will now be described in greater detail. The following example embodiments describe methods and apparatuses for the remote monitoring and assessment of implantable artificial heart pumps without internal flow sensors. These example embodiments rely on indirect measurement of blood flow and blood pressure characteristics to guide decision-making regarding the optimum operating parameters of the machine.

FIG. 1 portrays an example comprehensive remote monitoring system 10 for an indirect-flow, implantable left ventricular assist device (LVAD) 60. The system may include a remote diagnostic device 20 that connects to the LVAD 60, a remote server 70 and an end-user device 80. LVAD 60 includes an inlet port that may be surgically positioned in the left ventricle of a patient's heart to receive oxygenated blood from the patient's lungs and an outflow port that may be surgically connected to the patient's aortic artery to conduit this blood to the patient's systemic circulation. LVAD 60 further includes an internal heart pump 62 to drive the flow of blood from the patient's lungs through the LVAD 60 to the patient's aortic artery. Depending on the particular configuration of the LVAD 60, the internal heart pump 62 may comprise a rotating element supported with mechanical bearings, electromagnetic energy, or a combination thereof.

The internal heart pump 62 is designed to communicate with the external environment through a driveline that exits the patient's body from an incision in the patient's chest wall to accommodate the receipt of electricity from an external power supply 66. Depending on the configuration of the LVAD 60, the power supply 66 may comprise one or more elements configured to produce the electricity that powers the internal heart pump 62. Depending on the particular configuration of the LVAD 60, the power supply 66 may comprise a battery that provide direct current electricity, a wall outlet or other source that provides alternating current electricity.

The driveline also enables receipt of a motor control objective from an external heart pump controller 64, which may, for instance, direct a rotating element of the internal heart pump 62 to rotate at a particular speed. In turn, the rotating element of the internal heart pump 62 may be configured to adjust its power consumption either up or down to maintain this predefined rotation speed despite changes in the patient's hemodynamic or physiological status that influence the environmental propulsion favorability. At least one computer-readable storage medium may store software comprising a set of program code instructions that, when executed, causes the heart pump controller 64 to continuously monitor power consumption by the rotating element of the internal heart pump 62 and to detect fluctuations that may occur over time. Moreover, the software may utilize a proprietary, machine-specific algorithm to estimate blood flow through the internal heart pump 62. This algorithm can, for instance, be based on the known engineering principle that correlates power and speed to flow, the viscosity of the patient's blood that affects fluid dynamics, and motor design idiosyncrasies.

As noted previously, the majority of LVADs do not utilize actual flow probes that are inserted in the implanted device due to the physiological problems such probes could cause. Instead, LVADs generate indirect flow measurements based on the machine-specific computational algorithms that report the flow rate variable based on its mathematical relationship of the known, observed variable of motor speed set by the operator and certain known patient physiological characteristics such as blood viscosity to the real-time power fluctuations of the machine (e.g., in terms of the wattage pulled by the machine from the battery or other power source) as it maintains a constant set speed under dynamic hydraulic conditions. The machine-specific algorithm referenced above may, in this regard, be derived by in vitro modeling of the functioning of a given LVAD using mock fluid loops that replicate the operation of the device in a fluid-filled, circulatory environment. Specifically, by establishing a computer connection to the LVAD, the data it generates when it is in communication with the internal pump component during dynamic activity in the mock loop can be collected, then software can be used to reconstruct the unique attributes of an LVAD's machine-specific algorithm that are based on how its proprietary motor(s) is designed to propel blood through the heart. This deduced algorithm can be used to indirectly measure blood flow through a given internal heart pump 62.

The diagnostic device 20 may be attached to the heart pump controller 64 through a compatible mechanical and electrical connector port 50, which will be described in greater detail below in connection with FIGS. 2A-2D and 3A-3D. As illustrated in FIGS. 2A-2D and 3A-3D, the diagnostic device 20 is a portable and in some embodiments, hand-holdable, device that does not appreciably interfere with the controller's physical profile or with a patient's pre-existing mobility, activity level, or range of motion (it should be understood that in embodiments in which the heart pump controller 64 is configured to wirelessly transmit data in lieu of a diagnostic device 20 will not substantially affect the overall morphology of the heart pump controller 64 itself and thus will also not interfere with a patient's pre-existing mobility, activity level, or range of motion). Once connected to the heart pump controller 64 via connector port 50, the diagnostic device 20 can receive data from the heart pump controller 64. In some embodiments, this connector port 50 only allows data transfer in a downstream direction, such that data cannot be sent from the diagnostic device 20 to the patient's heart pump controller 64; preventing data from being uploaded to the patient's heart pump controller 64 in this fashion protects the integrity of the software employed by the heart pump controller 64 and, in turn, ensures that changes to the operating speed of the LVAD 60 can only occur with manual adjustment. However, in other embodiments it may be conceivable that the connector port 50 allows data to be transferred in both directions. For instance, the connector port 50 may include a user authentication feature (e.g., a biometric screening element or other secure identification mechanism) that allows data to be uploaded to the heart pump controller 64 by pre-authorized users.

When the diagnostic device 20 receives data from the heart pump controller 64 via the connector port 50, a bus within the diagnostic device 20 (e.g., LVAD data format interface and router 22) stores the data in a memory device 25. Microprocessor 24 may remove patient-identifying information and may encrypt the data to protect health information before it is transmitted to a remote server 70 for analysis.

After processing the data, the diagnostic device 20 may make the data accessible to additional devices. In this regard, the data can be transmitted using a wireless transmitter 28 and internal antenna 29. The transmitter 28 may, in various embodiments, have the capability to transmit collected data using a wide variety of wireless transmission modes 30 (e.g., wireless communication modes such as radio communication, optical communication, sonic communication or the like). One example transmission may communicate data using special radio frequencies designated only for medical communications. It will be understood that while wireless transmission modes are contemplated herein and illustrated in FIG. 1, some example embodiments of the diagnostic device 20 may additionally or alternatively interact with remote devices (e.g., remove server 70) using wireline communication.

The data that is retrieved by the diagnostic device 20 and transmitted to remote server 70 may include speed setting input, estimated instantaneous and average blood flow rate over a specified time interval, variable power consumption, indications regarding the incidence of any proprietary pre-programmed alarm notifications, or any other data that the LVAD 60 is configured to collect. Data transmission from the wireless diagnostic device 20 to a remote server 70 would typically be configured to occur continuously to facilitate the early identification of data trends that might require intervention. In an alternative configuration, however, diagnostic device 20 may be configured to transmit data periodically, on a scheduled basis, or in response to an ad hoc request initiated from the server 70.

While not true of all embodiments contemplated herein, the functions of the diagnostic device 20 may in some cases be supported by an integrated power supply 26. The power supply 26 in such arrangements may be configured to receive power from the heart pump controller 64, regulate it to compatible voltage, and allocate the power to the router 22, processor 24, and wireless transmission components 28 and 29.

Figure 2A:
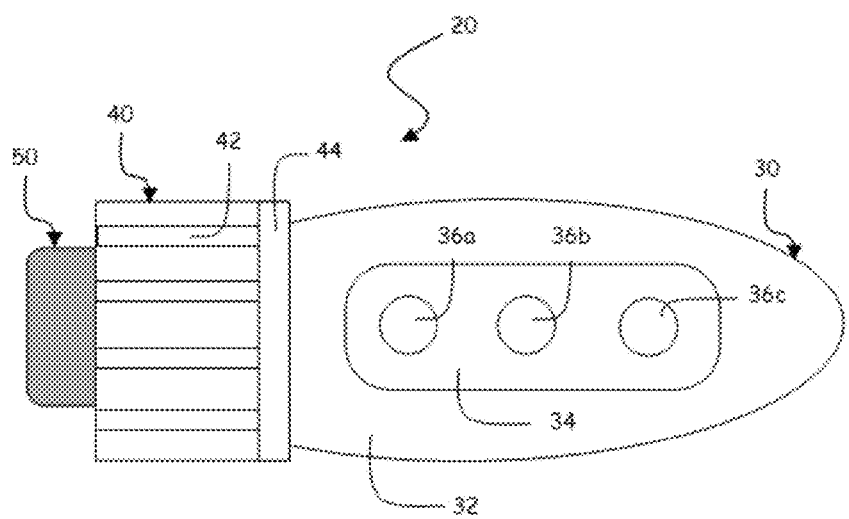
Figure 2B:
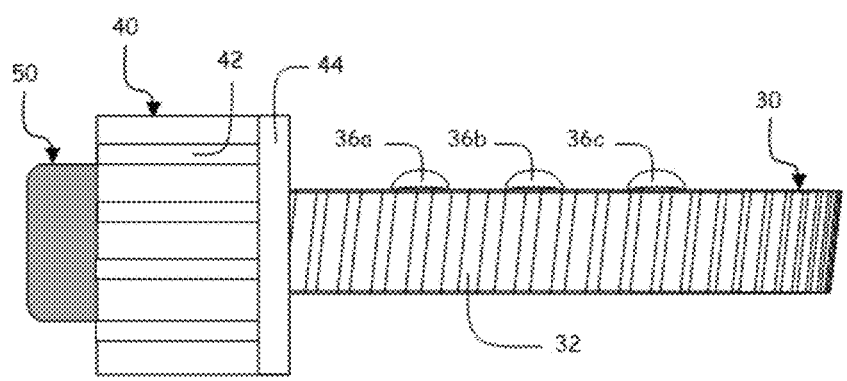
Figure 2C:
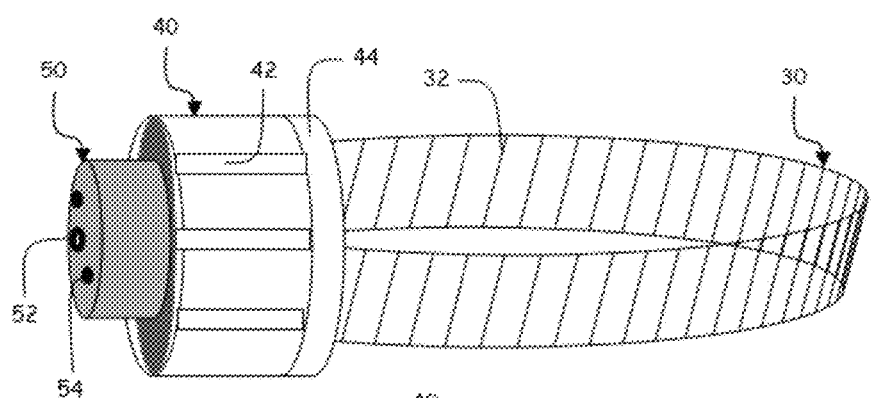

FIG. 2A depicts a long-axis, top-down view of diagnostic device 20. FIG. 2B depicts the same device in long-axis side view, and FIG. 2C depicts the same side view with a downward tilt and medial rotation. As illustrated in FIGS. 2A, 2B, and 2C, the diagnostic device 20 includes a posterior portion 30. In some embodiments, the main enclosure of the electrical components 32 is composed of injection-molded plastic, although other materials may also be considered without departing from the spirit or scope of the present invention.

Figure 2D:
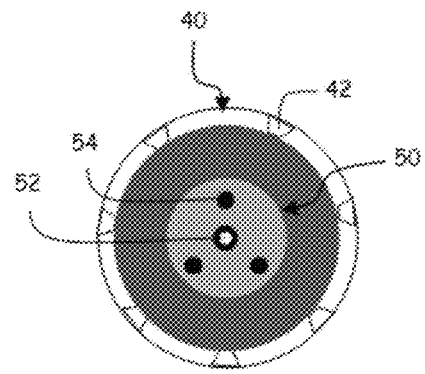

The upper portion of the main enclosure 32 may include a faceplate 34 (which may, in some embodiments, be polycarbonate) with display sensor data lights that indicate various things. In some embodiments, the faceplate may include three display sensor data lights to indicate whether functioning contact exists between the heart pump controller and device (e.g., via display element 36a), whether there is active communication between the device and a remote network (via display element 36b), and whether a recent alarm has been received from the controller (via alarm display element 36c), respectively. In some embodiments, a communication disruption (either between the diagnostic device 20 and heart pump controller 64 or between the diagnostic device 20 and remote server 70) or the incidence of controller alarms may be indicated with a colored light (e.g., a red light). It should be understood that while alarm display element 36c may illustrate whether a recent alarm has been received from the controller of the LVAD 60, in some embodiments, alarm display element 36c may additionally or alternatively illustrate whether an alarm condition is received from remote server 70, as described below. In contrast, normal connection and internal heart pump 62 function may be indicated with a differently colored like (e.g., a green light). As mentioned previously, the diagnostic device 20 also includes a female connector port 50 (which may, for instance, be rubber) having a central recessed hole 52 surrounded by three symmetrically-arranged peripheral recessed holes 54. Protecting the connector port 50 is an injection molded plastic shroud 40. Shroud 40 may comprise a hub 44, and central bevels 42 that twist into position to secure the contact points between the diagnostic device 20 and heart pump controller 64. FIG. 2D displays the diagnostic device 20 in a short-axis frontal view, illustrating this hub and shroud configuration.

Figure 3A:
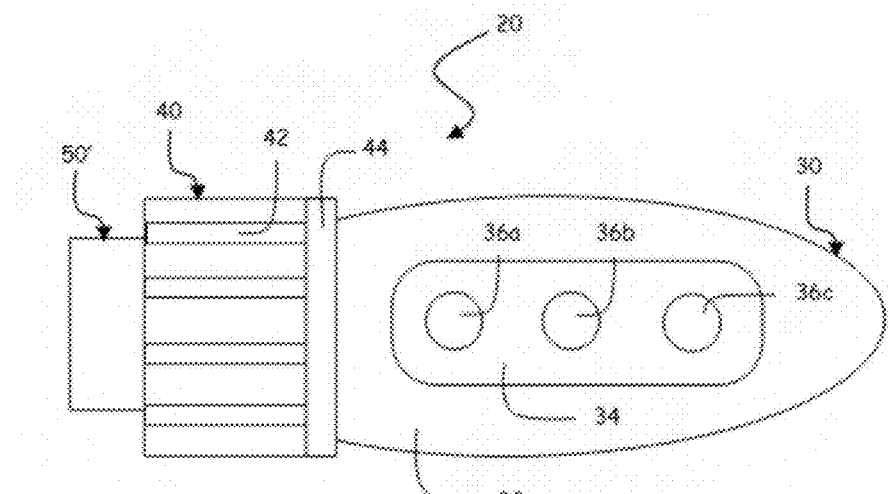
Figure 3B:
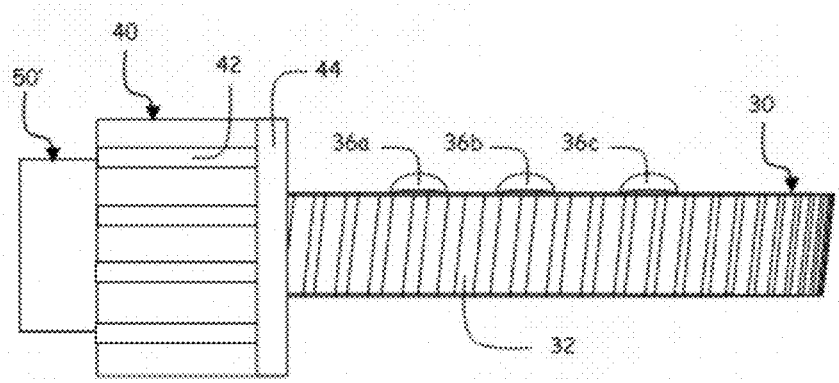
Figure 3C:
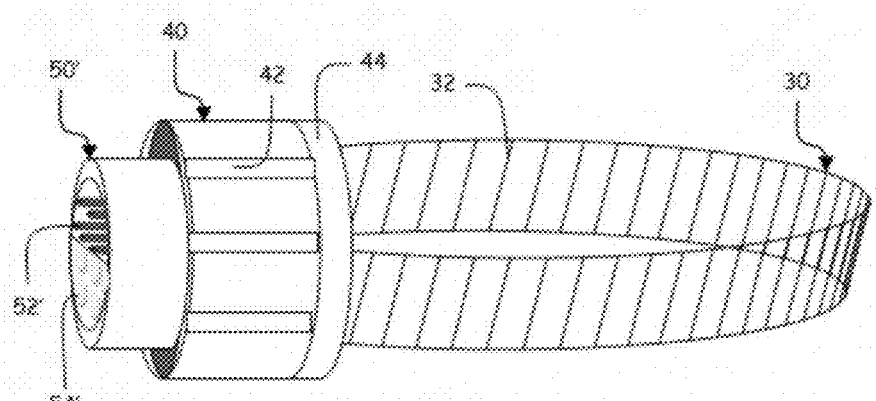
Figure 3D:
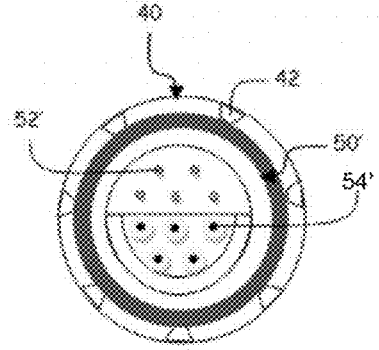

An alternative embodiment of this diagnostic device is displayed in FIGS. 3A-3D. These figures reproduce the same device enclosure 32, display elements 36a-36c, and plastic connector shroud 40 as displayed in FIGS. 2A-2D, and in the same sequence of orientations. FIG. 3D displays the diagnostic device 20 in short-axis frontal view, portraying connector port 50' that consists of two panels comprising a male and a female component. The superior portion of the panel is comprised of six pins 52' and an inferior portion comprised of six recessed holes 54'. Accordingly, FIGS. 2A-2D differ from FIGS. 3A-3D only in that FIGS. 3A-3D illustrate a different connector port 50' that enables the diagnostic device 20 can connect to and communicate with a different type of heart pump controller 64 that uses a different interface. Specifically, while the connector port 50 illustrated in FIGS. 2A-2D is configured to interface with the heart pump controller 64 of an HVAD system (manufactured by HeartWare), the connector port 50' illustrated in FIGS. 3A-3D is configured to interface with the heart pump controller 64 of a HeartMate II LVAD (manufactured by Thoratec). However, it will be understood that while diagnostic device 20 has been illustrated in FIGS. 2A-2D and 3A-3D using these two particular types of connector ports 50 and 50', other types of connector ports configured to interface with other heart pump controllers are contemplated without departing from the spirit or scope of the present invention.

As noted previously, it should be understood that the capabilities of the diagnostic device 20 may in some embodiments be added to the heart pump controller 64 itself. In such embodiments, the heart pump controller may thus wirelessly transfer heart pump performance data without the need to connect to a separate diagnostic device 20 that acts as an intermediary.

Once data has been transmitted by the wireless diagnostic device 20 (or, in embodiments in which the heart pump controller 64 itself is able to communicate wireless, once data has been wirelessly transmitted by the heart pump controller 64), it may be received by telecommunications hardware (e.g., antenna 71) of a remote server 70. Once received by the server 70, the data may be conveyed by a bus (e.g., data router 72) to the processor 74 for formatting and analysis, and stored in the memory device 77 of the server 70 for future retrieval and use. The data can be analyzed using a variety of bioengineering algorithms to calculate the performance characteristics of the internal heart pump 62.

For instance, in addition to remotely obtaining and monitoring LVAD flow characteristics as described above, this data can also be used to derive the difference in pressure between the outlet portion of the internal heart pump 62 in the patient's proximal ascending aorta and the inflow portion of the internal heart pump 62 in the patient's left heart chamber. As with the machine-specific algorithm referenced previously, machine-specific algorithms can illustrate pressure differences between the inlet port and outflow ports of the LVAD 60. This pressure differential may be estimated, for instance, using the polynomial equations described in Table 2 in Salamonsen et al., *Response of Rotary Blood Pumps to Changes in Preload and Afterload at a Fixed Speed Setting Are Unphysiological When Compared With the Natural Heart*, 35 Artificial Organs E47, E49 (2011), the entire contents of which are incorporated herein by reference. Having access to this pressure difference variable is of great medical value because it represents a dynamic relationship between the heart and systemic circulation that changes according to the phase of contraction of the heart, the degree of constriction of the vasculature, and the current state of total body fluid balance. Depending on the particular software used and the configuration of adjunctive traditional non-invasive physiological measurements not specific to LVAD patients, the real-time state of total body fluid balance can be further deduced from the total pressure difference. Timely and frequent access to this information thus facilitates the judicious administration of medications to ensure that they are maintained in a healthy state of equilibrium.

In addition, the data received by the remote server 70 may be conveyed via a communication network 400 (e.g., the Internet) to a modem 82 of an end-user device 80. The end-user device 80 may be configured to present a graphical user interface (e.g., computer screen/interface application 100) to a user 90 for viewing the performance characteristics of the internal heart pump 62. It should be understood that in some embodiments, the end-user device 80 may be the remote server 70, and in such embodiments, the end-user device 80 need not retrieve data from the server 70 via a communication network 400.

FIG. 4 illustrates a flowchart containing a series of operations for analyzing data retrieved from an implanted artificial heart pump that indirectly measures flow. More specifically, FIG. 4 provides a functional block diagram describing the analysis of data captured by the diagnostic device from the heart pump and the physiological variables that can be estimated with software applications. The data received from the internal heart pump 62 can be reconfigured and made available to the end-user 90 as a management decision-support tool with prediction capabilities. The operations illustrated in FIG. 4 may, for example, be performed by, with the assistance of, and/or under the control of the devices utilized in comprehensive remote monitoring system 10, which include LVAD 60, diagnostic device 20, server 70, and end-user device 80.

In operation 402, the heart pump controller 64 receives data representative of the fixed speed setting that is entered from the internal heart pump 62 and estimates the rate at which blood is flowing through the machine. As noted previously, given the dynamic nature of the motor's power utilization at a certain speed, the heart pump controller 64 can use a proprietary algorithm to perform this estimation.

In operation 404, a diagnostic device 20 connected to the heart pump controller 64 retrieves this data from the heart pump controller 64 and transmits it to a remote server 70 for analysis and further processing. As one aspect of this operation, the diagnostic device may remove patient-identifying information and/or encrypt the data to protect health information before the data is transmitted to a remote server 70 for analysis. It will be understood that in embodiments in which the heart pump controller 64 itself can wirelessly transmit data, operation 404 may instead be performed by the heart pump controller 64 itself.

In operation 406, the remote server 70 executes software (e.g., data analysis software 76, which may be stored in memory device 77) to use the flow data to create real-time flow waveform graphs illustrating phasic waveforms including individual peaks and troughs representing the data retrieved from the LVAD 60. It should be understood that the diagnostic device 20 is configured to transmit the retrieved data to the remote server 70 either prior to operation 406 or as an initial aspect of operation 406. Moreover, it should also be understood that the remote server 70 may cache specific heart pump performance characteristics using a data storage device (e.g., memory device 77) for a specified period of time prior to overwriting.

In operation 408, the server 70 further executes software (e.g., software 76) to utilize the waveform amplitude morphology over time to estimate the pump flow pulsatility (a heart pump function variable that varies according to the amount of blood in the heart's left ventricle).

In operation 410, the server 70 further executes software (e.g., software 76) to derive the difference in pressure between the outlet portion of the internal heart pump 62 in the patient's proximal ascending aorta and the inflow portion of the internal heart pump 62 in the patient's left heart chamber. In some embodiments, the software can further use adjunctive traditional non-invasive physiological measurements not specific to LVAD patients to assess the real-time state of total body fluid balance for the patient by estimating the pressure in the patient's left heart during its relaxation phase before the beginning of each beat (a crucial physiological parameter that can be used to determine the medication regime required to optimize heart function and circulatory health).

In operation 412, the server 70 may further execute software (e.g., software 76) to estimate the pressure difference between the arterial pressure at the distal end of the internal heart pump 62 (e.g., at the outlet port) and the left ventricle pressure in the proximal end of the internal heart pump 62 (e.g., the inflow port) and thus arrive at an approximation of the patient's blood pressure during the different phases of the heartbeat.

Finally, in operation 414, after having estimated all of these cardiac indices, the server 70 may further execute software (e.g., software 76) to track the changing nature of the patient's cardiovascular status and anticipate the nature of support required to optimize the function of the heart pump.

After analysis, the server 70 may locally store the processed data and analysis results or transmit the data and results to a centralized series of data services and data storage units for subsequent access by multiple end-users 90 with password clearance. In some embodiments, these end-users 90 may be located at off-site locations and who may thus access the data and/or analysis results via an Internet connection and modem 82. These designated end-users 90 can retrieve this data via communication network 400 using a computer software application that further arranges the data visually on the screen in a format that is medically intuitive and will facilitate positive or negative trend recognition, as discussed in connection with FIG. 5. In other embodiments, end-users 90 may access the data and/or analysis results using server 70 itself (and in such embodiments, the server 70 may comprise the end-user device 80, as noted previously.

In some embodiments, if the data and/or analysis results fall outside of predefined thresholds (and in this regard, these thresholds may be previously identified by clinicians or may be based on similarities between the data or analysis results and historical data or analysis results known to be associated with poor patient outcomes), an alarm condition may be transmitted back to the diagnostic device 20, which may in turn alert the patient to consult a clinician for a recommended course of action. Still further, such alarm conditions may additionally or alternatively be transmitted directly to medical professionals for immediate action (such as to prepare for the arrival of the patient at a medical facility or to dispatch responders to the patient's location for more immediate treatment or to communicate to the patient the nature of the alarm or any immediate clinical interventions that the patient can make unilaterally). As noted previously, the diagnostic device 20 (and/or heart pump controller 64) may include an element (e.g., alarm display element 36c or the like) configured to convey information regarding the alarm condition to the patient.

FIG. 5 provides an illustration of a user interface provided by an example remote heart pump monitoring application that provides a visual dashboard for assessing data acquired from a heart pump that measures flow indirectly and patient-related physiological estimates. In some embodiments, an end-user may view this user interface using any suitable terminal (e.g., a fixed device such as a desktop, or a mobile device, such as a laptop, PDA, tablet, smartphone, or the like). The remote heart pump monitoring application may feature motion graphics and animation that includes a visual estimate of the instantaneous blood flow through the heart pump in liters per minute (L/min) per seconds of time (s) 110, displayed in continuous waveform format 112 over a numerical grid 114 with a link to archival data 116 that provides statistical analysis of flow averages and identifies the instances in which flow values occurred outside of limit parameters stipulated by the end-user 90. The application may also depict a continuous graph 120 of the relationship between the systemic arterial pressure 122 and the left ventricular pressure 124 estimates in millimeters of mercury (mmHg). The remote heart pump monitoring application may also provide a link to archived data 126, including numerical trends. Another feature of the remote heart pump monitoring application may be a schematized drawing of a heart pump-cardiac unit 130 with movement depictions to represent blood flow and machine function and numerical display of the real-time estimates of the left ventricular volume 132 and flow through the pump 134, and speed setting and power consumption 136. In some embodiments, the remote heart pump monitoring application also includes additional links to particular patient-care related categories. For accessing additional useful patient information, the display may include a related grouping section 140 with a link to archived patient laboratory results 142, medical history 144, and cardiac diagnostic imaging and dynamic studies 146. For urgent medical and engineering problems, the display may include a related grouping section 150 with a retrieval link to the local emergency medical services 152 and physician 154 and engineer 156 consultation.

FIG. 6 illustrates a high-level system diagram in one example embodiment described herein. As shown in FIG. 6, implanted LVAD pump machinery that measures flow indirectly (e.g., internal heart pump 62) is connected through a driveline that exits the patient's body from an incision in the patient's chest wall to connect to an external heart pump controller 64. In turn, a diagnostic device 20 may connect to the heart pump controller 64 and may wireless transmit data to a remote server (not shown), which may cause communication of a graphical interface providing the data and analysis results to an end-user in the form of a visual software application 100. By virtue of the wireless connection provided by the diagnostic device 20, this example embodiment facilitates the communication of data regarding the functioning of the implanted device to medical professionals and the ability to identify and react to abnormal indicators that would otherwise be undetectable outside of a medical facility. As a result, this example embodiment (and others described herein) greatly expands the oversight capability and more data-driven optimization of indirect flow measurement blood pumps without added interference with recipients' quality of life or independence.

As described herein, example embodiments of the present invention provide a system enabling the acquisition of data generated by implanted indirect flow measurement artificial heart pumps in an outpatient setting. Heretofore, this real-time data has been inaccessible to expert decision makers during the interval period that a patient is outside of a formal medical environment, but utilizing embodiments of the present invention, indirect flow measurements and other pump performance characteristics may now be remotely retrieved. Moreover, example embodiments enable the transmission of that data for expert review and provide software applications for characterizing pump performance using a visual display feature that depicts real-time estimates of the patient's circulatory status to assess physiological needs and promote positive long-term clinical outcomes. In turn, example embodiments of the present invention promote best-practice clinical decisions regarding heart pump use than currently exist for indirect flow measurement machines.

It will be understood that although the above example embodiments are described in connection with a heart pump 62 that indirectly measures blood flow because indirect-flow devices represent the vast majority of heart pumps in use, other embodiments are also contemplated herein for remote monitoring of heart pumps that directly measure blood flow. In such embodiments, the structure and functions of the diagnostic device 20 parallel those of the example embodiments discussed above, with the caveat that the data conveyed wirelessly by the diagnostic device 20 is received from a different type of heart pump (with a similar caveat for embodiments where the heart pump controller is used in lieu of a diagnostic device 20 to perform this wireless conveyance).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for managing an external heart pump controller of an implanted artificial heart pump using a portable diagnostic device physically attached to the external heart pump controller, the method comprising:

receiving data at the portable diagnostic device from the external heart pump controller via one or more electrical connections at a connector port of the portable diagnostic device, wherein the external heart pump controller is incapable of wireless data transmission, wherein the portable diagnostic device comprises a wireless transmitter, wherein the portable diagnostic device is configured to facilitate diagnosis of one or more faults of the implanted artificial heart pump, wherein the connector port is configured to physically attach the portable diagnostic device to the external heart pump controller, and wherein the connector port is further configured to facilitate transmission of data between the external heart pump controller and the portable diagnostic device; and initiating wireless transmission of the data from the portable diagnostic device to a server device via the wireless transmitter, wherein the data transmitted from the portable diagnostic device is indicative of one or more performance characteristics of the implanted artificial heart pump.

2. The method of claim 1 further comprising connecting the connector port of the portable diagnostic device to the external heart pump controller before receiving the data at the portable diagnostic device.

3. The method of claim 1 further comprising:

receiving an indication from the server device that the data transmitted from the portable diagnostic device falls outside a corresponding established numerical threshold parameter; and presenting an alert to at least one user in response to the indication.

4. The method of claim 1, wherein the one or more electrical connections at the connector port define a one-way electrical connection, such that the portable diagnostic device is configured to receive data from the external heart pump controller and the portable diagnostic device is incapable of transmitting data to the external heart pump controller.

5. The method of claim 1 further comprising removing patient-identifying information from the data received from the external heart pump controller prior to initiating transmission of the data to the server device.

6. The method of claim 1 further comprising continuously transmitting or periodically transmitting the data to the server device while the connector port is engaged with the external heart pump controller.

7. The method of claim 1, wherein the portable diagnostic device receives power from the external heart pump controller.

8. The method of claim 1 further comprising transmitting the data to the server device in response to a request initiated from the server device.

9. A non-transitory computer readable medium having computer program instructions stored therein for managing an external heart pump controller of an implanted artificial heart pump using a portable diagnostic device physically attached to the external heart pump controller, the instructions when executed by a processor are configured to cause the portable diagnostic device to:

receive data at the portable diagnostic device from the external heart pump controller via one or more electrical connections at a connector port of the portable diagnostic device, wherein the external heart pump controller is incapable of wireless data transmission, wherein the portable diagnostic device comprises a wireless transmitter, wherein the portable diagnostic device is configured to facilitate diagnosis of one or more faults of the implanted artificial heart pump, wherein the connector port is configured to physically attach the portable diagnostic device to the external heart pump controller, and wherein the connector port is further configured to facilitate transmission of data between the external heart pump controller and the portable diagnostic device; and initiate wireless transmission of the data from the portable diagnostic device to a server device via the wireless transmitter, wherein the data transmitted from the portable diagnostic device is indicative of one or more performance characteristics of the implanted artificial heart pump.

10. The computer readable medium of claim 9, wherein the instructions when executed by the processor are further configured to cause the portable diagnostic device to:

receive an indication from the server device that the data transmitted from the portable diagnostic device falls outside a corresponding established numerical threshold parameter; and present an alert to at least one user in response to the indication.

11. The computer readable medium of claim 10, wherein the alert comprises illuminating one or more lights on the portable diagnostic device.

12. The computer readable medium of claim 9, wherein the instructions when executed by the processor are further configured to cause the portable diagnostic device to:
cause the one or more electrical connections at the connector port to define a one-way electrical connection, such that the portable diagnostic device is configured to receive data from the external heart pump controller and the portable diagnostic device is incapable of transmitting data to the external heart pump controller.

13. The computer readable medium of claim 9, wherein the instructions when executed by the processor are further configured to cause the portable diagnostic device to:
remove patient-identifying information from the data received from the external heart pump controller prior to initiating transmission of the data to the server device.

14. The computer readable medium of claim 9, wherein the instructions when executed by the processor are further configured to cause the portable diagnostic device to:
continuously transmit or periodically transmit the data to the server device while the connector port is engaged with the external heart pump controller.

15. The computer readable medium of claim 9, wherein the instructions when executed by the processor are further configured to cause the portable diagnostic device to:
transmit the data to the server device in response to a request initiated from the server device.

16. The computer readable medium of claim 9, wherein the data transmitted from the portable diagnostic device is representative of a value related to the implanted artificial heart pump or a patient in which the artificial heart pump is implanted, the value comprising at least one of a motor speed setting, an estimated instantaneous blood flow rate, an average blood flow rate over a specified time interval, a variable power consumption, or a proprietary preprogrammed alarm condition notification.

17. The computer readable medium of claim 9, wherein the instructions when executed by the processor are further configured to cause the portable diagnostic device to:
transmit the data from the portable diagnostic device via radio frequencies allocated for exclusive medical usage.

18. The method of claim 1, wherein the implanted artificial heart pump is an indirect flow heart pump configured to indirectly measure blood flow, such that the data transmitted from the portable diagnostic device is indicative of one or more performance characteristics of the indirect flow heart pump.

19. The method of claim 1, further comprising receiving electrical power at the portable diagnostic device from the external heart pump controller, wherein the portable diagnostic device comprises a power supply, the power supply configured to regulate the electrical power received from the external heart pump controller to a compatible voltage for the portable diagnostic device.

20. The method of claim 1, further comprising:
receiving, at the server device, the data transmitted from the portable diagnostic device;
diagnosing one or more faults of the implanted artificial heart pump based on the received data, wherein diagnosing the one or more faults comprises:
calculating trend data based on the received data,
comparing the calculated trend data to one or more threshold parameters to determine the one or more faults of the implanted artificial heart pump, and
transmitting notification of the one or more faults to the portable diagnostic device.

* * * * *